United States Patent [19]

d'Argembeau

[11] Patent Number: 4,573,920
[45] Date of Patent: Mar. 4, 1986

[54] DEVICE FOR CLEANING THE PROXIMAL FACES OF TEETH

[76] Inventor: Etienne Y. d'Argembeau, Rue de Belle-Vue, 24, B - 1050 Bruxelles, Belgium

[21] Appl. No.: 601,822

[22] Filed: Apr. 19, 1984

[30] Foreign Application Priority Data

Apr. 29, 1983 [BE] Belgium ............................ 210669

[51] Int. Cl.[4] ............................................ A61C 3/00
[52] U.S. Cl. ................................ 433/141; 15/167 R
[58] Field of Search ................ 15/167 R; 128/62 A; 132/93; 433/141

[56] References Cited

U.S. PATENT DOCUMENTS

| | | | |
|---|---|---|---|
| 1,624,054 | 4/1927 | Kuhne | 132/93 |
| 1,929,530 | 10/1933 | Abelson | 15/167 R |
| 2,386,085 | 10/1945 | Babel | 132/93 |
| 2,476,201 | 7/1949 | Ligoure | 128/62 A |
| 2,819,482 | 1/1958 | Applegate | 15/167 R |
| 4,128,910 | 12/1978 | Nakata et al. | 15/167 R |

Primary Examiner—John J. Wilson
Attorney, Agent, or Firm—Sughrue, Mion, Zinn, Macpeak and Seas

[57] ABSTRACT

The present invention relates to a device for cleaning the proximal faces of teeth.

The present device comprises a handle to which is fixed at least one elastically deformable cleaning element in the form of a thin bed. This cleaning element may consist of at least one layer, or at least one series of bristles, the plane of symmetry of which is preferably substantially perpendicular to the longitudinal axis of the handle.

4 Claims, 8 Drawing Figures

DEVICE FOR CLEANING THE PROXIMAL FACES OF TEETH

BACKGROUND OF THE INVENTION

The present invention relates to a device for cleaning the mesial and distal faces or the proximal faces of teeth, that is the facing surfaces of two adjacent teeth.

It is known that the proximal faces of teeth are often the seat of disease, particularly caries. Therefore it is advisable to keep the proximal faces of teeth as clean as possible, all the more because fragments of food are often retained there.

The use of tooth-picks is known for dislodging fragments of food from the gaps between adjacent teeth. Tooth-picks are most certainly effective for this purpose, but they do not allow the facing surfaces of adjacent teeth to be cleaned. The use of waxed textile thread is known to this end, which is moved upwards and downwards after it has been introduced between two adjacent teeth. The use of thread of this type is very time-consuming because after the thread has been introduced between two adjacent teeth, it has to be moved from the apical plane of the teeth towards the gun or vice versa, in order to thoroughly sweep across the proximal faces of the teeth. The use of virtually conical brushes in the shape of a rat's tail is also known for cleaning the proximal faces of adjacent teeth. These known brushes are often relatively ineffective because in many cases the gap between the proximal faces of adjacent teeth is too small to allow the bristles of these brushes which are embedded in the end of a support to pass through.

SUMMARY OF THE INVENTION

The present invention sets out to overcome the disadvantages of known devices and an object thereof is a device for cleaning the proximal faces of adjacent teeth, characterised in that it comprises in particular at least one elastically deformable element forming a thin bed which is fixed to a handle.

The elastically deformable element may, according to the present invention, consist of a thin layer or at least a series of essentially parallel bristles.

In one particular embodiment of the present invention, the device has two elastically deformable elements each of which is formed by a series or bed of bristles and which are positioned parallel to each other, these elements projecting from an essentially flat or slightly convex surface of the handle and preferably being perpendicular thereto. Each series or bed of bristles may comprise one or more rows of bristles, the plane of symmetry of which is preferably substantially perpendicular to the longitudinal axis of the handle.

Adjacent bristles may be advantageously joined to each other in places, such as at the free ends thereof and/or elsewhere.

As regards the spacing between the series of bristles, it is preferably substantially equal to the maximum interdental width, that is the spacing between the proximal faces of two adjacent teeth at the point where these faces are furthest away from each other, that is at the shoulders of adjacent teeth or at the base of the interdental triangle. This spacing is generally from about 1.5 to 3 mm.

The height of the cleaning elements from the handle which supports them is preferably at least equal to the radius of the largest circumference delimited by the largest teeth (molar teeth).

Other characteristics and details of the present invention will be revealed from the following description of the accompanying drawings which diagrammatically show, by way of example only, several embodiments of the device according to the present invention.

BRIEF DESCRIPTION OF THE DRAWINGS

In the various Figures which show the devices according to the present invention larger than in real life, the same reference numerals relate to the same elements.

DETAILED DESCRIPTION

Figure 1:
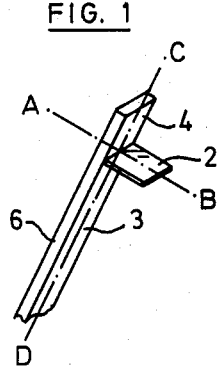
FIGS. 1 and 2 are perspective views of two embodiments of a device according to the present invention for cleaning the proximal faces of teeth.

The device for cleaning the proximal faces of adjacent teeth which is shown in FIG. 1 comprises an elastically deformable element consisting of a thin, elastically deformable layer or sheet 2, for example of plastics material (such as nylon), which is fixed to a handle 3 constituted by a small rod which may be of plastics material, of wood, of metal or of any other material. The layer or sheet 2 should be rigid enough to be introduced into the space between two adjacent teeth and to allow the proximal faces of these teeth to be brushed or cleaned by following the convex shape of these faces.

As can be seen in FIG. 1, the plane of symmetry A-B of the layer which constitutes the cleaning element 2 of the device is substantially perpendicular to the longitudinal axis C-D of the handle 3, although this plane A-B may form an angle slightly different to 90° with the axis C-D.

Figure 2:
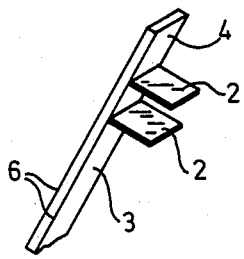

A variant of the device shown in FIG. 1 is shown in FIG. 2. Two substantially parallel thin sheets or layers 2 are used in this variant. These layers 2 may be from 0.1 to 0.2 mm thick and may be from 5 to 8 mm in height from the surface 4 of the handle 3 to which they are attached. The spacing between these layers may be from about 1.5 to 3 mm.

Figure 3:
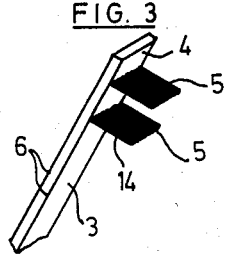
FIG. 3 is a similar view to that in FIG. 1 and shows a third embodiment of the device according to the present invention.
Figure 4:
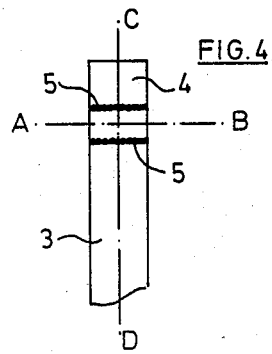
FIG. 4 is a front view of the device shown in FIG. 3.

A third embodiment of the device according to the present invention is shown in FIGS. 3 and 4, and comprises two parallel series or beds of bristles 5 which are fixed to the surface 4 of the handle 3, and this surface may be flat or slightly convex. Although each series or bed of bristles 5 which is shown in FIGS. 3 and 4 only has one row of bristles, it is possible, in relation to the present invention, for each series or bed of bristles, to have two or more than two rows of bristles, and the bristles of one row may possibly be staggered with respect to those of the one or more adjacent rows. As can be seen in FIG. 4 the plane of symmetry of the series or beds of bristles 5, which is indicated by a dash-dotted line A-B, is substantially perpendicular to the longitudinal axis C-D of the handle 3.

In FIGS. 1 to 3, the handle 3 has a substantially rectangular transverse cross-section and sharp longitudinal edges 6. It is clear that the shape of the handle 3 may vary and that the edges thereof should preferably be rounded. The handle is advantageously several centimeters long, and may be, for example, from 5 to 10 cm. The length of the handle should be such that the user may reach the gaps between the teeth of the lower and upper jaw and the lingual side and the vestibular side and the back of the gum groove which covers the rear surface of the back molar teeth with the one or more layers 2 or the series of beds of bristles 5.

Figure 5:
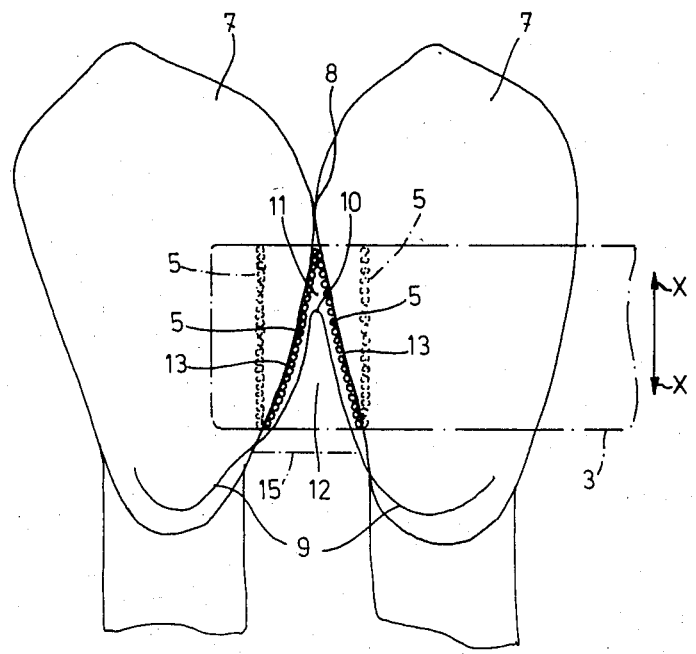
FIG. 5 is a diagrammatical view which partially shows the device shown in FIGS. 3 and 4 when it is used to clean the proximal faces of two adjacent teeth.

FIG. 5 shows, in large scale, two adjacent teeth 7 which contact each other at 8. The line 9 represents the free edge of the gum, the interdental ridge of which is shown by 10. FIG. 5 shows the position occupied by the two parallel beds of bristles 5 (shown by the dotted line) before the device is used. This Figure also shows that when the two beds of bristles 5 are introduced into the interdental space 11 situated below the contact point 8 and which forms the interdental triangle indicated by 12, the bristles 5 of the two parallel beds apply themselves to the facing proximal faces 13 of the teeth 7, following the shape of these faces 13. The beds of bristles 5 diverge from the contact point 8 of the teeth 7 towards the gum 9, as can be clearly seen in FIG. 5. While the beds of bristles 5 are applied thus to the proximal faces 13 of the teeth 7, they are moved up and down in the direction of arrows X—X, so that the lateral faces of the bristles 5 of the two beds sweep across the proximal faces 13 of the teeth thereby cleaning these faces.

Figure 6:
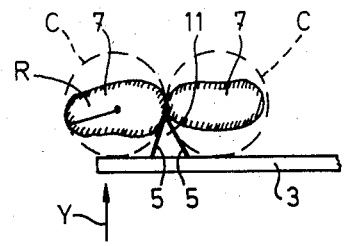
FIG. 6 is a plan view from above of two adjacent teeth with the device according to FIGS. 3 and 4 in the operating position with the bristles inserted between the teeth.

The inflexion which the bristles of the two beds of bristles 5 are given when they have been introduced into the interdental space 11 in the direction of arrow Y can be seen in the plane view of FIG. 6.

The ends of the bristles 5, which are remote from the ends which are fixed to the handle 3, may be free (that is separated from each other) or be joined to each other within each bed of bristles 5. The bristles 5 may also be locally joined in other places to each other.

The spacing between the parallel series or beds of bristles 5 is preferably substantially equal to the maximum interdental width, that is equal to the length of the base 15 of the interdental triangle 12 (c.f. FIG. 5), this width being in practice from about 1.5 to 3 mm.

As regards the height of the bristles 5 from the surface 4 of the handle 3, they are preferably at least equal in height to the radius R (c.f. FIG. 6) of the largest circumference C which is delimited by the largest teeth, and this circumference essentially corresponds to the crowns of the teeth 7 which are shown in FIG. 6.

The bristles (which may be of plastics material, such as nylon) of the beds of bristles 5 which are shown in FIGS. 3 to 6 may have a cross-section of from 0.1 to 0.3 mm and each bristle may be of a monofilament or polyfilament nature.

Figure 7:
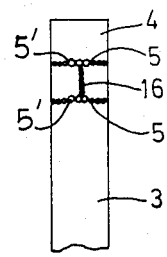
FIGS. 7 and 8 are large-scale front views and show two other embodiments of the device according to the present invention.

FIG. 7 shows another embodiment of the device according to the present invention, in which the handle 3 has two rows or beds of bristles 5, and some of the bristles which are indicated by reference numerals 5' have a larger transverse cross-section than others, for the purpose of making the beds of bristles 5 more rigid.

According to the present invention, the device comprising two layers or beds of parallel bristles is provided with means for keeping them apart from each other. In the embodiment which is illustrated in FIG. 7, these means consist of a series of bristles 16 which extends transversely from the beds of bristles 5 to these beds of bristles.

Figure 8:
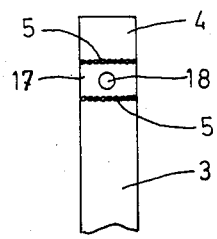

An embodiment of the present invention similar to that in FIG. 7 is shown in FIG. 8, except that the means for separating the beds of bristles 5 from each other and firmly applying these beds of bristles 5 to the lateral proximal faces of two adjacent teeth when the device is being used consists of one or more jets of water or another fluid which are introduced into the gap 17 between the beds of bristles 5 by one or more holes 18 which are provided in the handle 3, the one or more holes 18 being linked to a conduit (not shown) which is provided in the handle and connected to a pressurised fluid source, such as water or air.

It is clear that the invention is not limited to the above-mentioned details and that numerous modifications may be made to these details within the scope of the present invention.

Thus, the free end of the one or more layers 2 or bristles 5 may be tapered or rounded to facilitate the insertion thereof into the interdental space.

I claim:

1. A device for cleaning the curved proximal side faces of teeth, comprising: an elongate handle (3), and two rectangular elastically deformable sheets (2) attached by one edge, opposite free edges thereof, to the handle, said sheets being disposed parallel to each other and each having a plane of symmetry which is substantially perpendicular to a longitudinal axis of the handle, the distance between two adjacent sheets being such that, when these sheets are pressed against the side face of two adjacent teeth, the free edges of both of said sheets follow the curved proximal faces of the two adjacent teeth and penetrate into the space between said adjacent teeth, wherein said distance between two adjacent sheets is less than the width of the smallest teeth, and is 1.5 to 3.0 mm.

2. The device according to claim 1, in which the two adjacent sheets are in contact with each other when these sheets are fully introduced in the space between said adjacent teeth.

3. A device for cleaning the curved proximal side faces of teeth, comprising: an elongate handle (3), and two rows (5) of elastically deformable bristles attached by one end, opposite free ends thereof, to the handle, said rows of bristles being disposed parallel to each other and each having a plane of symmetry which is substantially perpendicular to a longitudinal axis of the handle, the distance between two adjacent rows of bristles being such that, when these rows of bristles are pressed against the side face of two adjacent teeth, the free ends of both of said rows follow the curved proximal faces of the two adjacent teeth and penetrate into the space between said adjacent teeth, wherein said distance between two adjacent rows of bristles is less than the width of the smallest teeth, and is 1.5 to 3.0 mm.

4. A device according to claim 3, in which the two adjacent rows of bristles are in contact with each other when these rows are fully introduced in the space between said adjacent teeth.

* * * * *